United States Patent
Youssefi et al.

(10) Patent No.: US 8,588,487 B2
(45) Date of Patent: Nov. 19, 2013

(54) FAST ALGORITHM FOR STREAMING WAVEFRONT

(75) Inventors: Gerhard Youssefi, Landshut (DE); Hans-Joachim Polland, Wolfratshausen (DE)

(73) Assignee: Bausch & Lomb Incorporated, Rochester, NY (US)

( * ) Notice: Subject to any disclaimer, the term of this patent is extended or adjusted under 35 U.S.C. 154(b) by 315 days.

(21) Appl. No.: 12/866,122

(22) PCT Filed: Mar. 13, 2009

(86) PCT No.: PCT/EP2009/052995
§ 371 (c)(1),
(2), (4) Date: Aug. 4, 2010

(87) PCT Pub. No.: WO2009/112575
PCT Pub. Date: Sep. 17, 2009

(65) Prior Publication Data
US 2011/0007945 A1   Jan. 13, 2011

(30) Foreign Application Priority Data
Mar. 14, 2008 (DE) .......................... 10 2008 014 294

(51) Int. Cl.
*G06K 9/00* (2006.01)
*G01J 1/20* (2006.01)
*A61B 3/14* (2006.01)

(52) U.S. Cl.
USPC ......... 382/128; 382/100; 250/201.9; 351/206

(58) Field of Classification Search
USPC ................. 382/100, 127; 351/211, 212, 206; 250/201.9
See application file for complete search history.

(56) References Cited

U.S. PATENT DOCUMENTS

| | | | | |
|---|---|---|---|---|
| 2003/0086063 | A1* | 5/2003 | Williams et al. | 351/221 |
| 2007/0273828 | A1* | 11/2007 | Polland et al. | 351/204 |
| 2008/0259279 | A1* | 10/2008 | Pettit et al. | 351/246 |

FOREIGN PATENT DOCUMENTS

| | | |
|---|---|---|
| DE | 10333558 A1 | 3/2005 |
| DE | 60104236 T2 | 7/2005 |
| DE | 69737242 T2 | 10/2007 |
| EP | 1450671 B1 | 2/2008 |

* cited by examiner

*Primary Examiner* — Anand Bhatnagar
*Assistant Examiner* — Soo Park
(74) *Attorney, Agent, or Firm* — Toan P. Vo; Denis A. Polyn

(57) ABSTRACT

The invention is generally directed to the field of image processing, and more particularly to a method and an apparatus for determining a wavefront of an object, in particular a human eye. The invention discloses a method and an apparatus for real-time wavefront sensing of an optical system utilizing two different algorithms for detecting centroids of a centroid image as provided by a Hartmann-Shack wavefront sensor. A first algorithm detects an initial position of all centroids and a second algorithm detects incremental changes of all centroids detected by said first algorithm.

22 Claims, 6 Drawing Sheets

FAST ALGORITHM FOR STREAMING WAVEFRONT

The invention is generally directed to the field of image processing, and more particularly to a method and an apparatus for determining optical properties of an object, in particular a human eye.

Hartmann-Shack wavefront sensors are currently recognized of being the state of the art for determining a wavefront of an object, particularly of a human eye, even if a few other concepts such as the Tracy wavefront sensor are based on different concepts, e.g., the Tscherning principle. A Hartmann-Shack wavefront sensor typically includes a microlens array that images portions of a non-distorted or distorted wavefront exiting the eye onto a CCD detector/camera. The image produced by the microlens array, as exemplarily illustrated in FIG. 1, comprises an array of small dots of light called centroids on a predetermined location. In case of an aberrated wavefront at least some centroids are displaced from reference locations of the light dot image. The displacements of the centroids are related to the localized slopes of the wavefront exiting the eye's pupil. Zernike polynomials or other mathematical tools are used to derive from theses displacements of the centroids from their pre-defined positions aberration parameters of an eye. In order to provide higher levels of resolution, the development of the wavefront sensors in the past led to an increasing number of centroids for determining a more accurate wavefront error.

In principle the following steps are conducted to acquire and display wavefront aberration data. Firstly, an image is captured by a camera and the obtained data are analyzed, i.e. the positions of the centroids are determined. From this analysis of the centroid image, i.e. from the (dis-)placement of the centroids, a wavefront map is calculated and can be displayed. The critical step in terms of timing in this chain of steps is the analysis of the centroid image. The position of each individual centroid needs to be determined and particularly in the field of ophthalmology usually a sanity check is applied. The performance level in these steps, i.e. determination of centroid positions and sanity check, regarding the calculation time is directly dependent on the number of centroids to be analyzed.

It is well known that every single measurement of such a Wavefront aberration is a snap shot of the actual aberration configuration of the eye and that there is a dynamic in the aberration of the eye. This dynamic component is based on a variety of factors such as the ongoing micro accommodation of the lens, the micro movements of the eye and even the cardiac cycle. Therefore it is desirable to have a "streaming wavefront" concept which means in other words to have a real-time wavefront sensing by which the actual wavefront error is captured, analyzed and finally displayed in real-time to provide the base for either an averaging of the Wavefront data for a certain time interval or to apply said sanity check to ensure that the final aberration data used for any further applications are representative for the general state of the examined eye. The increasing number of centroids, however, leads to a higher amount of processing operations and thus to an increased processing time. Thus, the concept of having a real time wavefront and therefore a minimized processing amount is critical for the mentioned reasons above.

The present invention aims to provide a method and an apparatus for determining a resulting wavefront from a centroid image with a reduced processing amount, regardless of the specific technical details of the apparatus. This object is achieved by the features of the claims.

The invention discloses a method and an apparatus for real-time wavefront sensing of an optical system utilizing at least two different algorithms for detecting centroids. According to an aspect of the invention, a first algorithm detects an initial position of all centroids and a second algorithm detects incremental changes of centroids detected by said first algorithm.

A first centroid image is acquired and analyzed for determining the positions of preferably all centroids using said first centroid determining algorithm. From a subsequently acquired centroid image the positions of the centroids are determined using said second centroid determining algorithm, wherein said second centroid determining algorithm determines the position of each centroid with reference to the position of the respective centroid in the first and/or foregoing acquired centroid image. The second centroid determining algorithm is faster than the first centroid determining algorithm since not the whole image must be analyzed for potential centroid positions. Preferably only a predetermined area in the vicinity of a previously determined centroid is searched by the second centroid determining algorithm.

According to an aspect of the invention, the time consuming centroid position detection using the first centroid determining algorithm is applied once at the beginning of the streaming wavefront acquisition. After the positions have been detected once, only the positional changes in the following images are tracked to determine the centroid locations and the resulting wavefront. Determining the positional changes as accomplished by the second centroid determining algorithm results in a decreased data processing amount and thus the calculation time decreases.

Due to the features of the invention it is possible to significantly improve the reliability of the wavefront determination and to increase processing speed of measurements. According to a further aspect of the invention two or more measurements, even many hundreds of measurements can be averaged. Thus, measurements can be compensated which are caused by statistical accommodation, i.e. measurements are evaluated which show the maximum value in the spherical equivalent. Alternatively or additionally eye fluctuations and saccades can be determined and eliminated. According to an aspect of the invention, wavefront maps can be seen online which, e.g., allows to adjust an injection laser to a location where disturbing effects are eliminated. As an example the wavefront might be disturbed if the most aberrated corneal region of a keratoconus is hit by the injection laser.

The invention describes a general concept which is independent of the basic algorithm which is used to detect the fundamental centroid positions and therefore can be applied to a variety of existing wavefront sensors. The algorithm is preferably applied to lenslets with a small focal length, e.g. below 10 mm. In this case the changes of the centroid positions from image to image are usually not large.

These and other objects of the present invention will become more readily apparent from the following detailed description. However, it should be understood that the detailed description and specific examples, while indicating the preferred embodiments of the invention, are given by way of illustration only, since various changes and modifications within the scope of the invention will become apparent to those skilled in the art based upon the description and drawings herein and the pending claims.

FIG. 3b illustrates the crosshairs shown in FIG. 3a;

FIG. 4b illustrates crosshairs located onto the centroids as shown in FIG. 4a;

Figure 1:
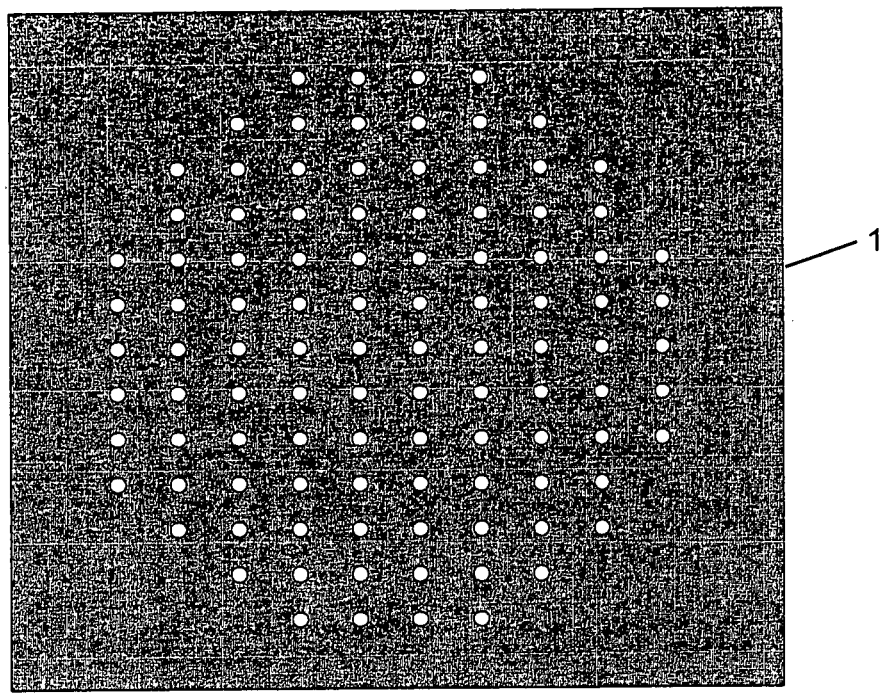
FIG. 1 shows an exemplary centroid image of a Hartmann-Shack sensor.

In FIG. 1 an exemplary centroid image of a Hartmann-Shack wavefront sensor is shown, which is captured by a camera. The measurement object in case of FIG. 1 can be either considered as a reference object without aberrations or centroids which populate the optimised pre-calculated positions for a non aberrated Wavefront exam, since neighbouring centroids 1 have constant distances in x and y direction, respectively. This example was used for clarification as the starting point for the described concept of the invention. According to the invention the starting image can also be an aberrated Wavefront exam.

Figure 2A:
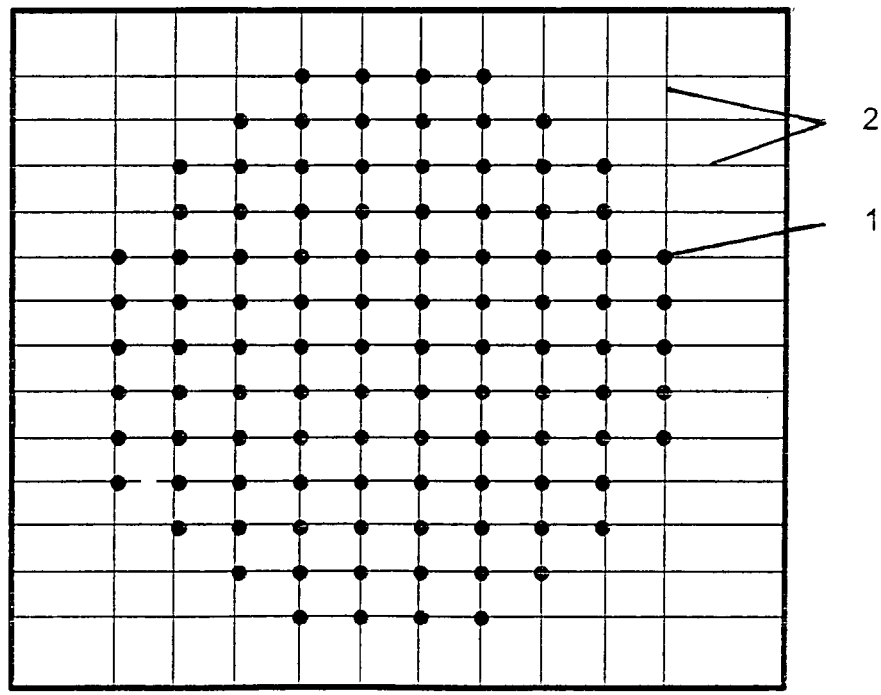
FIG. 2a shows a centroid image according to FIG. 1 located on a grid.
Figure 2B:
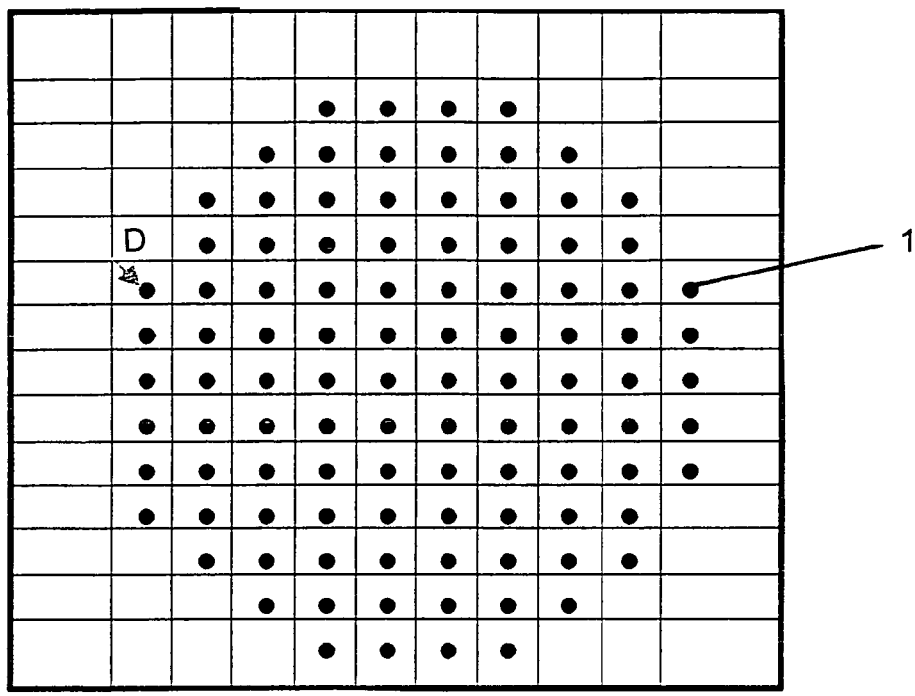
FIG. 2b shows a centroid image according to FIG. 2a with a global movement of the centroids.

FIG. 2a illustrates a centroid image with grid lines 2 in x and y direction, wherein the centroids 1 as shown in FIG. 1 are located on the intersection points of the grid lines 2. FIG. 2b shows a global movement of the centroids 1 as illustrated in FIG. 2a towards a specific direction indicated by arrow D. Such a global movement of the centroids 1 may be due to intrinsic fluctuations on the dynamic inside of the eye (clear lens, IOP variations, etc.) as well as tear film variations, which may vary and cause fluctuations. According to a preferred embodiment of the invention an average of a series of images is provided to compensate for such fluctuations in order to improve the reliability of the wavefront reading.

The invention may also be applied to the monitoring of an accommodation response of an optical system to a kind of accommodation stimulus.

The invention uses the fact that centroids 1 will show a positional deviation from their position in a previously acquired image to a following acquired image, but the actual shift is within a certain range. The actual shift is basically given by the focal length of the sensor and the expected changes in the wavefront. Upon initially determining the positions of the centroids 1 with a first centroid determining algorithm only a predetermined area relating to the direct neighbourhood of the locations which have been recognized for the first centroid position are searched by a second centroid determining algorithm. Preferably, any following next centroid image is handled in the same way by the second centroid determining algorithm.

Figure 3A:
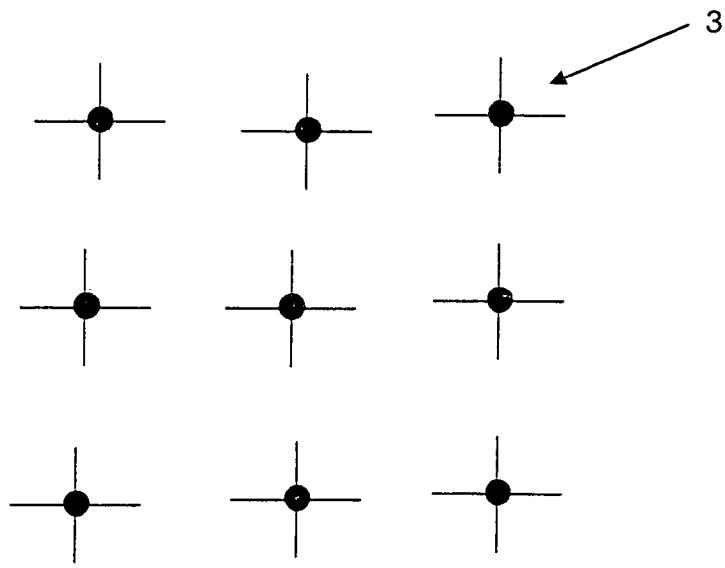
FIG. 3a illustrates crosshairs located on determined centroid positions.
Figure 3B:
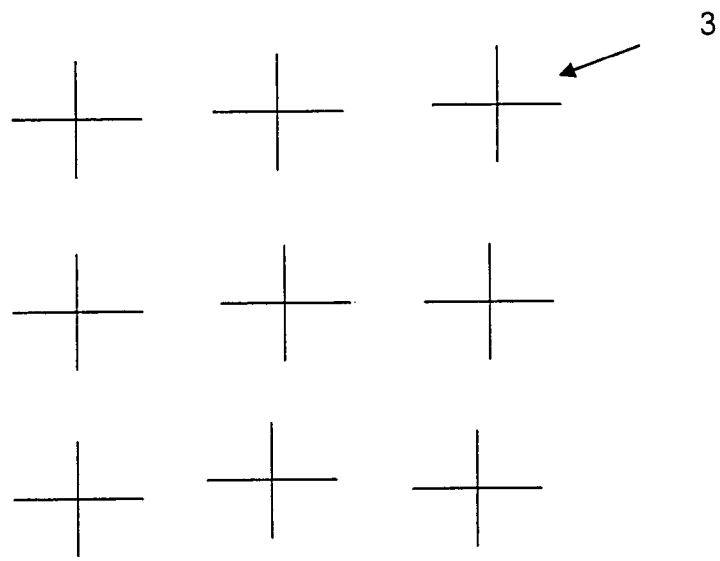
Figure 3C:
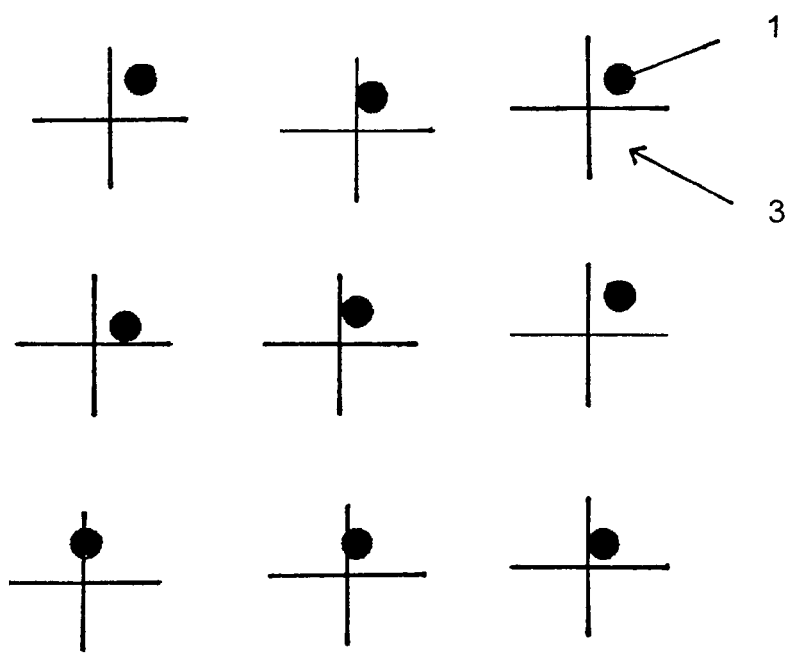
FIG. 3c illustrates crosshairs shown in FIG. 3b and respective new captured centroids.

FIG. 3a shows a subset of centroids 1 of a centroid image corresponding to an eye to be analyzed. It shall be noted that the following method is applied to all centroids 1 of a centroid image and reference is made to the subset of centroids only to simplify the description of the invention. The initial centroid position, which is determined by the first centroid determining algorithm is marked by respective crosshairs 3. The positions of the centroids 1 indicated as crosshairs 3 only in FIG. 3b are preferably stored in a storage medium, which may be the memory allocated by a software application. The centroid positions of the same subset of centroids of a following acquired centroid image as shown in FIG. 3c will differ from the stored centroid positions but the centroids 1 will not show a significant displacement. This difference may be the result of any change of the eye to be analyzed, for example a different accommodation status of the eye.

Therefore, the search algorithm determining the centroid positions from any centroid image except for the initial determination can be limited to a region around the first and/or foregoing position for the search to detect the new centroid positions. This limited region to be searched decreases the total time needed to identify the new positions, since it leads to reduced processing amount.

Figure 4A:
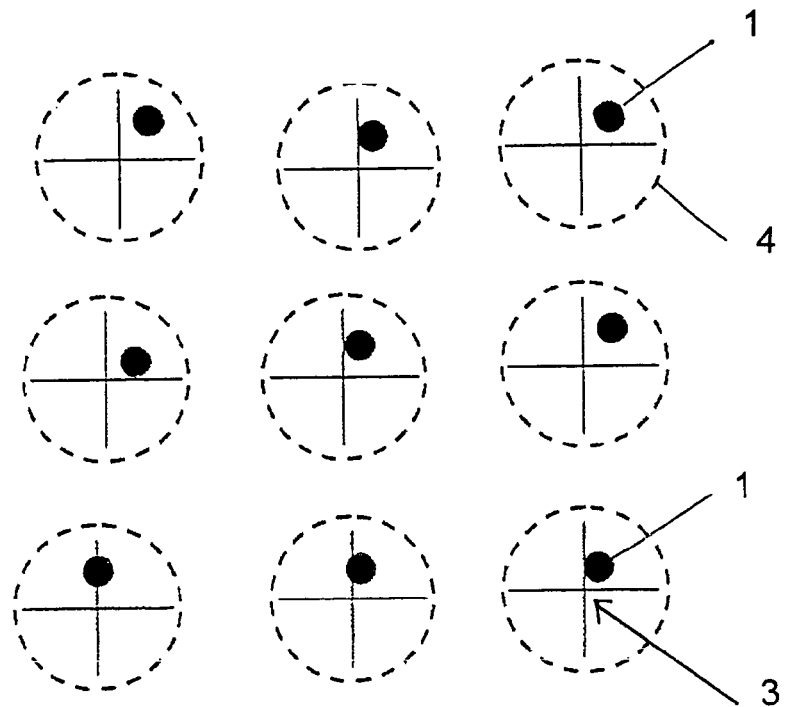
FIG. 4a illustrates crosshairs and centroids according to FIG. 3c and the analyzed area of each crosshair.
Figure 4B:
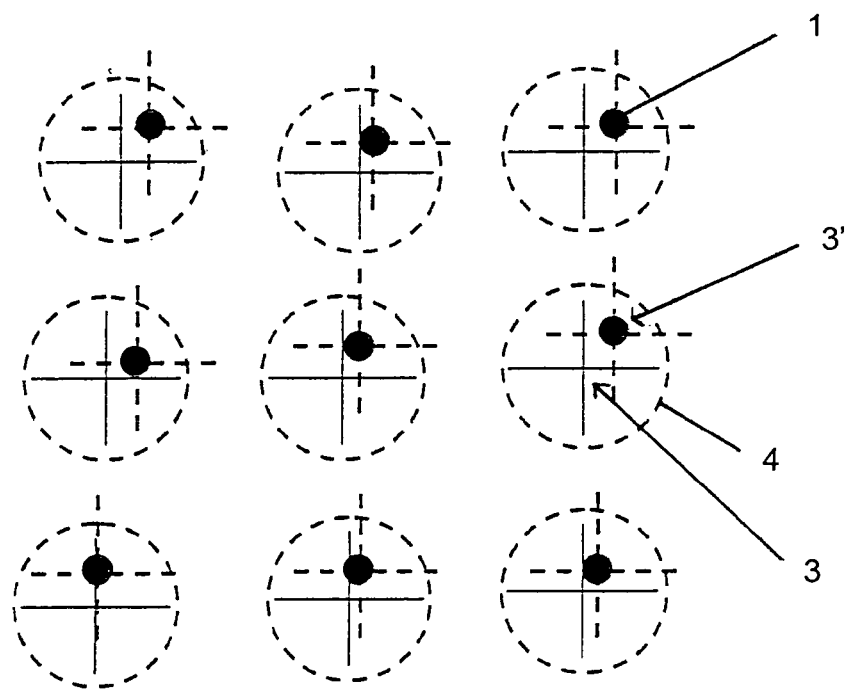
Figure 4C:
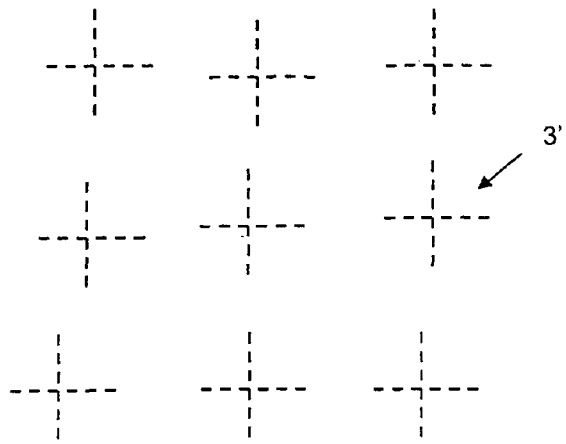
FIG. 4c illustrates crosshairs relating to the centroid positions shown in FIG. 4b.

In FIG. 4a crosshairs 3 and the positions of the centroids 1 are the same as in FIG. 3c. In addition, a predetermined search area defining an area 4 within the vicinity of each centroid is illustrated as a circular area around each crosshair. The vicinity area 4 may have other forms and/or sizes. The centroids 1 relating to a next/following centroid image lies within the vicinity area 4 and can thus be detected with the second centroid determining algorithm. In a further step, which is illustrated in FIG. 4b, crosshairs 3' are placed on the determined centroid position of the centroids 1 shown in FIG. 4a. The new identified positions will be used to create a new wavefront aberration map. Afterwards the positions of the crosshairs 3' as shown in FIG. 4c are used as the starting point for the next determination of the centroid positions, wherein the before-mentioned steps being described with reference to FIGS. 3b to 4c are repeated. At that time another difference of centroid positions may be present which may be the result of a further change of the eye to be analyzed, for example a further accommodation of the eye.

If one or more centroids 1, e.g. a predetermined percentage, are located outside the vicinity area 4, i.e. cannot be located by the second centroid determining algorithm, preferably a new centroid image is captured and analyzed by the second centroid determining algorithm. In case a predetermined number of subsequent centroid images cannot be analyzed by the second centroid determining algorithm, preferably the first centroid determining algorithm is applied to analyze a centroid image and thus provide a new basis for using the second centroid determining algorithm when analyzing subsequent centroid images.

The vicinity area 4, relating to the area adjacent to the position of a centroid in the first and/or foregoing centroid image is the direct neighbourhood being preferably determined by a deviation dx and dy. The deviation dx, dy determining the neighbourhood of a position of a centroid in the first and/or foregoing centroid image preferably amounts to 0.1% to 10% of the distance X of two neighbouring centroids in the x-direction and the distance Y of two neighbouring centroids in the y-direction, respectively. This vicinity area may have the form of a circle, rectangle or other suitable description of the neighbourhood of a centroid.

Figure 5:
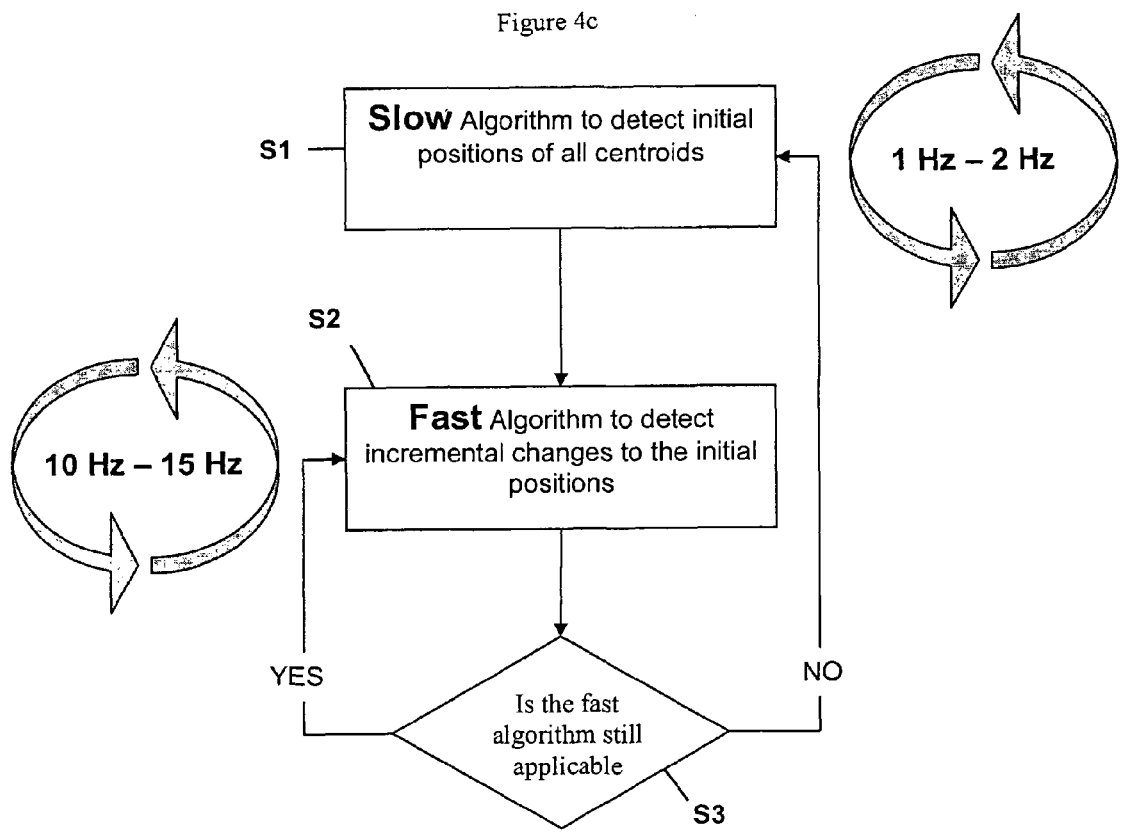
FIG. 5 shows the basic concept of utilizing a first slow algorithm providing the basis for a second fast algorithm in accordance with the invention.

In FIG. 5 the general concept of the invention is illustrated. In a first step S1 a slow algorithm corresponding to the above discussed first centroid detecting algorithm detects initial positions of all centroids of a centroid image. In this initial determination the whole centroid image as provided by a camera is analyzed, which means a high processing amount.

A tact cycle of the first centroid detecting algorithm may lie in the range of 1 Hz to 2 Hz which is too slow for real time Wavefront sampling. After the detection of the initial positions of all centroids a fast algorithm relating to the above discussed second centroid detecting algorithm is applied in step S2 to the following centroid image to detect incremental changes of all centroid positions in relation to the initial centroid positions. A tact cycle of the second centroid detecting algorithm may lie in the range of 10 Hz-15 Hz which is significantly faster than the first tact cycle. The before-mentioned tact cycles are examples and may vary depending on system parameters, in particular the computing time for performing a slow algorithm and a fast algorithm. Then, a check is performed in step S3 whether the fast algorithm is still applicable based on certain parameters, e.g., whether a new captured centroid 1 is located within the vicinity area 4 of a respective centroid 1 in a foregoing captured centroid image. In the affirmative (S3-Yes path), a new centroid image is acquired and analyzed by the fast algorithm. In case the fast algorithm is not applicable anymore (S3-No path), the slow algorithm is applied to again detect initial positions of all centroids.

Figure 6:
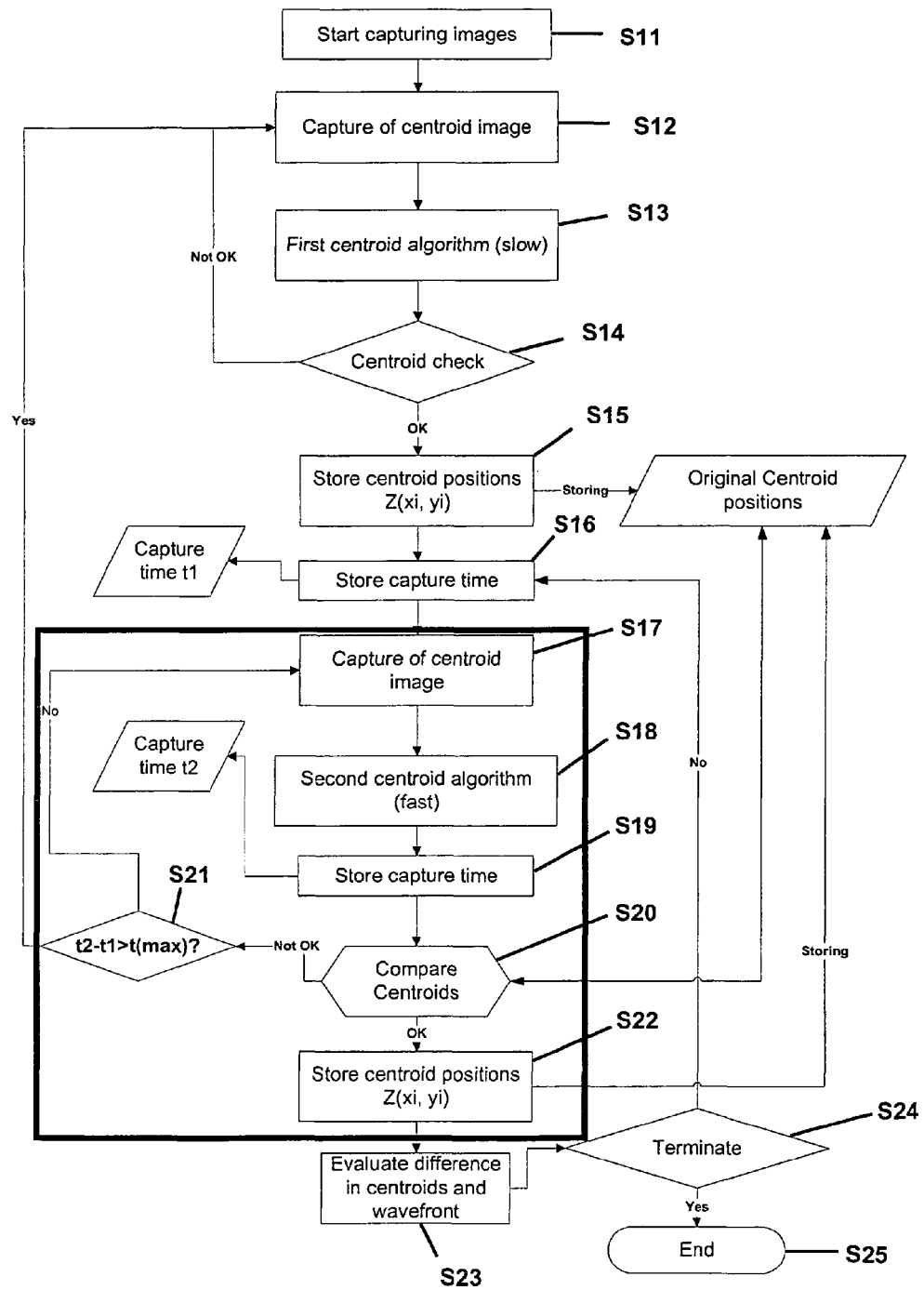
FIG. 6 illustrates a flow chart of a method according to the invention.

FIG. 6 provides a more detailed flow chart of an aspect of the invention and will be discussed in the following. The method starts in step S11. After capturing of a centroid image in step S12, a first centroid algorithm is applied in step S13 to detect the initial positions of all centroids 1. The first centroid algorithm analyzes the whole centroid image. Then, a centroid check is applied in step S14, wherein the basic quality of the acquired centroid image is evaluated. Typical acceptance criteria may be based on the eye to be analyzed for example that the size of the examined pupil is larger than 3.0 mm and/or that the size of a potential centroid gap inside the centroid group is smaller than 0.5 mm in diameter. Additional criteria may be image noise, background level or absolute number of detectable centroids. In case the centroid check fails (S14-NotOK path) the method continues at step S12 and a new centroid image will be captured. Further at step S13 the first centroid algorithm will be applied. Otherwise (S 14-OK path), the determined centroid positions $Z(x_i, y_i)$ will be stored in step S15 as original centroid positions. In step S16 the capture time t1 corresponding to the previously determined centroid positions $Z(x_i, y_i)$ will be stored.

The following steps S17 to S22 indicated as a block in FIG. 6 relate to the cycle of steps which is executed in case the first centroid detecting algorithm does not need to be applied. In step S17 a further centroid image is captured and analyzed by the second centroid determining algorithm in step S18. In step S18 preferably the new position of each centroid as determined in step S13 is determined. Preferably, the second centroid determining algorithm determines the position of a centroid in the next centroid image, as acquired in step S17, by searching in an area adjacent to the position of the respective centroid in the first and/or foregoing centroid image, i.e. in the vicinity area 4. As mentioned before, a tact cycle of the second centroid determining algorithm may lie in the range of 10 Hz to 15 Hz, which is about 10 times faster than the first centroid determining algorithm. Generally, the factor between the different computing times may be in a range of 2 to 100, preferably 5 to 20.

After step S19 storing the capturing time t2 relating to the previously determined centroids in step S18 the positions of the centroids as determined by the second centroid determining algorithm are compared to the stored original centroid positions and/or the stored foregoing centroid positions in step S20. In case the deviations do not exceed a predetermined value (S20-OK path), i.e. the centroids are located in the vicinity area 4 of a former determined centroid as discussed, e.g., with reference to FIG. 4a, the centroid positions as determined by the second centroid algorithm are stored in step S22. Then, the difference of the centroids and the wavefront is evaluated in step S23. In step S23 the difference in centroids and wavefront is evaluated, i.e., changes of the wavefront $\Delta W(x, y)$ are determined on the basis of the changes of the centroid positions for each following centroid image. In a decision step S24 it is decided whether the method is to be terminated and ends in step S25 or to be continued with step S16. Then in step S16 a capture time t1 relating to the centroid positions stored in step S22 is stored.

In case the comparison in step S20 of the centroid positions as determined by the second centroid algorithm and the original centroid positions shows that the deviation exceeds a predetermined value (S20-NotOK path), then step S21 follows. In step S21 it is determined whether within a pre-given time any further succeeding centroid image deviates more than the pre-given tolerance, i.e., whether t2-t1>t(max), whereas t(max) is the pre-given maximum time. If this time limit is not exceeded (S21-No path) the method will continue in step S17 and capture a further centroid image which will be analyzed by the second centroid algorithm. In case it is determined in step S21 that the maximum time is outrun (S21-Yes path), the method will proceed in step S12 and capture a new centroid image which will be analyzed by the first centroid determining algorithm. As mentioned above with reference to FIG. 4, another criteria can be that a predetermined number of subsequent centroid images cannot be analyzed by the second centroid determining algorithm. Thus, in step S21 it can be checked whether the number of attempts to analyze subsequent centroid images using the second algorithm is equal to a predetermined number $n_{max}$, wherein $n_{max}$ may be in a range of 2 to 50, preferably 4 to 25 and most preferably about 10.

While certain embodiments have been chosen to illustrate the invention, it will be understood by those skilled in the art that changes and modifications can be made without departing from the scope of the invention as defined in the appended claims.

The invention claimed is:

1. A method for real-time wavefront sensing of an optical system comprising the following steps: (a) acquiring a first centroid image and determining the positions of the centroids in said first centroid image using a first centroid determining algorithm; (b) acquiring a next centroid image and determining the positions of the centroids in the next centroid image using a second centroid determining algorithm, wherein said second centroid determining algorithm determines the position of each centroid with reference to the position of the respective centroid in the first centroid image, wherein the second centroid determining algorithm is an algorithm faster than the first centroid determining algorithm.

2. The method of claim 1, wherein the second centroid determining algorithm determines the position of a centroid in the next centroid image by searching in an area adjacent to the position of the respective centroid in the first centroid image.

3. The method of claim 2, wherein said area adjacent to the position of a centroid in the first centroid image is defined as the direct neighbourhood being determined by a deviation dx and dy.

4. The method of claim 3, wherein the deviation dx, dy determining the neighbourhood of a position of a centroid in the first centroid image amounts to 0.1% to 10% of the distance X of two neighbouring centroids in the x-direction and the distance Y of two neighbouring centroids in the y-direction, respectively.

5. The method of any of claims 1 to 4, further comprising the steps:
(c) acquiring a further centroid image and determining the positions of the centroids in the further centroid image using the second centroid determining algorithm, wherein the position of a centroid in the further centroid image is determined by reference to the position of the respective centroid in a previously acquired centroid image.

6. The method of claim 5, further comprising the step of comparing the positions of the centroids in a succeeding centroid image with the positions of the respective centroids in the first centroid image and if the deviation of the positions of the respective centroids is larger than a pre-given tolerance or if some centroids are lacking using the next succeeding centroid image.

7. The method of claim 6, further comprising the step of determining whether within a pre-given time any further succeeding centroid image deviates more than the pre-given tolerance, and evaluating the next centroid image with the first centroid determining algorithm if all further succeeding centroid images deviate more than the pre-given tolerance.

8. The method of claim 7, further comprising the step of determining changes of the wavefront $\Delta W(x, y)$ on the basis of the changes of the centroid positions for each following centroid image.

9. The method of claim 8, wherein said first centroid determining algorithm operates on a 1 Hz-2 Hz base.

10. The method of claim 9, wherein said second centroid determining algorithm operates on a 10 Hz-15 Hz base.

11. The method of claim 6, further comprising the step of determining changes of the wavefront $\Delta W(x, y)$ on the basis of the changes of the centroid positions for each following centroid image.

12. The method of claim 11, wherein said first centroid determining algorithm operates on a 1 Hz-2 Hz base.

13. The method of claim 12, wherein said second centroid determining algorithm operates on a 10 Hz-15 Hz base.

14. The method of claim 5, further comprising the step of determining changes of the wavefront $\Delta W(x, y)$ on the basis of the changes of the centroid positions for each following centroid image.

15. The method of claim 14, wherein said first centroid determining algorithm operates on a 1 Hz-2 Hz base.

16. The method of claim 15, wherein said second centroid determining algorithm operates on a 10 Hz-15 Hz base.

17. Apparatus for real-time wavefront sensing of an optical system comprising:
(a) acquiring means for acquiring centroid images;
(b) first determining means for determining the positions of the centroids in a first centroid image using a first centroid determining algorithm;
(c) second determining means for determining the positions of the centroids in a next centroid image using a second centroid determining algorithm, wherein said second centroid determining algorithm determines the position of each centroid with reference to the position of the respective centroid in the first centroid image, wherein the second centroid determining algorithm is an algorithm faster than the first centroid determining algorithm.

18. The apparatus of claim 17, wherein the second determining means is adapted to determine the position of a centroid in a further centroid image by reference to the position of the respective centroid in a previously acquired centroid image.

19. The apparatus of claim 17 or 18, wherein said first determining means operates on a 1 Hz-2 Hz base.

20. The apparatus of claim 19, wherein said second determining means operates on a 10 Hz-15 Hz base.

21. The apparatus of claim 18, wherein said second determining means operates on a 10 Hz-15 Hz base.

22. The apparatus of claim 17 wherein said second determining means operates on a 10 Hz-15 Hz base.

* * * * *